United States Patent
Weiguny et al.

(10) Patent No.: US 6,812,351 B2
(45) Date of Patent: Nov. 2, 2004

(54) HOLLOW CYLINDRICAL CATALYST AND A METHOD FOR PRODUCING A MALEIC ACID ANHYDRIDE

(75) Inventors: Jens Weiguny, Freinsheim (DE); Sebastian Storck, Mannheim (DE); Andreas Tenten, Maikammer (DE)

(73) Assignee: BASF Aktiengesellschaft, Ludwigshafen (DE)

(*) Notice: Subject to any disclaimer, the term of this patent is extended or adjusted under 35 U.S.C. 154(b) by 122 days.

(21) Appl. No.: 10/220,703

(22) PCT Filed: Mar. 6, 2001

(86) PCT No.: PCT/EP01/02492

§ 371 (c)(1), (2), (4) Date: Sep. 5, 2002

(87) PCT Pub. No.: WO01/68245

PCT Pub. Date: Sep. 20, 2001

(65) Prior Publication Data

US 2003/0114688 A1 Jun. 19, 2003

(30) Foreign Application Priority Data

Mar. 10, 2000 (DE) .......................... 100 11 307

(51) Int. Cl.⁷ ........................ C07D 307/60; B01J 27/188
(52) U.S. Cl. ...................... 549/259; 502/209
(58) Field of Search ................... 502/209; 549/259

(56) References Cited

U.S. PATENT DOCUMENTS

| | | |
|---|---|---|
| 4,283,307 A | 8/1981 | Barone |
| 4,713,464 A | 12/1987 | Fumagalli |
| 4,795,818 A | 1/1989 | Becker |
| 4,933,312 A | 6/1990 | Haddad |
| 5,095,125 A | 3/1992 | Haddad |
| 5,137,860 A | 8/1992 | Ebner |
| 5,158,923 A | 10/1992 | Barone |
| 5,168,090 A | 12/1992 | Ebner |
| 5,275,996 A | 1/1994 | Andrews |
| 5,296,436 A | 3/1994 | Bortinger |
| 5,641,722 A | 6/1997 | Mitchell |

FOREIGN PATENT DOCUMENTS

| | | |
|---|---|---|
| WO | 93/01155 | 1/1993 |
| WO | 95/26817 | 10/1995 |
| WO | 97/12674 | 4/1997 |

OTHER PUBLICATIONS

Chem. Eng. Sci, vol. 41, No. 4, 1986, 765–772, Wellauer et al.

*Primary Examiner*—Bernard Dentz
(74) *Attorney, Agent, or Firm*—Keil & Weinkauf

(57) ABSTRACT

A catalyst used in a process for preparing maleic anhydride by heterogeneously catalyzed gas-phase oxidation of a hydrocarbon having at least four carbon atoms by means of oxygen-containing gases comprises a catalytically active composition comprising vanadium, phosphorus and oxygen and has a essentially hollow cylindrical structure in which (a) the ratio of the height h to the diameter of the continuous hole $d_2$ is not more than 1.5 and (b) the ratio of the geometric surface area $A_{geo}$ to the geometric volume $V_{geo}$ is at least 2 $mm^{-1}$.

12 Claims, No Drawings

HOLLOW CYLINDRICAL CATALYST AND A METHOD FOR PRODUCING A MALEIC ACID ANHYDRIDE

This application is a 371 of PCT/EP01/02492, filed Mar. 6, 2001.

The present invention relates to a catalyst for preparing maleic anhydride by heterogeneously catalyzed gas-phase oxidation of a hydrocarbon having at least four carbon atoms, which comprises a catalytically active composition comprising vanadium, phosphorus and oxygen and has an essentially hollow cylindrical structure.

The present invention further relates to a process for preparing maleic anhydride by heterogeneously catalyzed gas-phase oxidation of a hydrocarbon having at least four carbon atoms using the catalyst of the present invention.

Maleic anhydride is an important intermediate in the synthesis of γ-butyrolactone, tetrahydrofuran and 1,4-butanediol, which are in turn used as solvents or are further processed to give, for example, polymers such as polytetrahydrofuran or polyvinylpyrrolidone.

The preparation of maleic anhydride by heterogeneously catalyzed gas-phase oxidation of hydrocarbons is generally carried out using pelletized catalysts, i.e. solid cylinders, comprising phosphorus, vanadium and oxygen. Such catalysts are described, for example, in the U.S. Pat. Nos. 5,275,996 and 5,641,722.

In the study on the partial oxidation of n-butane to maleic anhydride over catalysts comprising phosphorus, vanadium and oxygen reported by T. P. Wellauer et al., Chem. Eng. Sci., Vol. 41, No. 4, 1986, pages 765 to 772, it was found that rings having the geometry 8 mm×5 mm×5 mm (external diameter×height×diameter of the internal hole) display an about 65% higher heat removal from the catalyst bed per unit volume compared to the 3 mm×3 mm pellets (diameter×height) customarily used in industry. According to the simulations described, the yield of maleic anhydride can also be increased by 5–7% by use of the 5 mm×8 mm×5 mm rings ("hollow cylinders") rather than 2.5 mm×2.5 mm pellets ("solid cylinders").

A number of publications on the preparation of maleic anhydride by heterogeneously catalyzed gas-phase oxidation of hydrocarbons have described the use of catalysts comprising phosphorus, vanadium and oxygen and having an annular (hollow cylindrical) structure. Thus, U.S. Pat. No. 4,713,464 discloses rings having the geometry 5 mm×4 mm×2 mm, EP-A 0 593 646 discloses rings having the geometry 8 mm×8 mm×4 mm, U.S. Pat. No. 4,795,818 discloses rings having the geometry 6.35 mm×3.18 mm×3.18 mm and U.S. Pat. No. 5,296,436 discloses rings having the geometry 4.763 mm×4.763×1.588 mm.

U.S. Pat. No. 4,283,307 describes a catalyst structure comprising vanadium, phosphorus and oxygen and having the shape of a hollow cylinder whose external diameter is from 3.969 to 4.762 mm, whose height is 3.969 to 4.762 mm and whose internal diameter is from 0.888 to 7.925 mm. The diameter of the internal hole of the hollow cylinder is usually from 30 to 50% of the external diameter, with the height and external diameter preferably being equal. In the examples, a hollow cylindrical structure having the geometry 3.969 mm×3.969 mm×1.587 mm is disclosed. Compared to 3.969 mm×3.969 mm pellets having an identical active component, an increase in yield of maleic anhydride of up to 24% relative was obtained when using the hollow cylinders.

U.S. Pat. No. 5,168,090 discloses a catalyst structure for the preparation of maleic anhydride by heterogeneously catalyzed gas-phase oxidation of hydrocarbons which has at least one ordered cavity in the outer surface, a geometric volume $V_{geo}$ of from 30 to 67% of the theoretical volume $V_{overall}$ which the cavity-free, solid structure of the same external diameter and the same height would have and a ratio of the geometric surface area $A_{geo}$ to the geometric volume $V_{geo}$ of at least 20 cm$^{-1}$. The hollow cylinders described as a comparative example have a height of 4.76, 4.29 and 4.14 mm, an external diameter of 4.76 mm in each case and an internal diameter of 1.58 mm in each case.

It is an object of the present invention to find a catalyst for the preparation of maleic anhydride by heterogeneously catalyzed gas-phase oxidation of hydrocarbons which is easy to produce, displays a low pressure drop together with sufficiently high mechanical stability and makes possible a high hydrocarbon throughput over the catalyst compared to the catalysts of the prior art and at the same time makes possible a high conversion, a high selectivity, a high yield and therefore a high space-time yield.

We have found that this object is achieved by a catalyst for preparing maleic anhydride by heterogeneously catalyzed gas-phase oxidation of a hydrocarbon having at least four carbon atoms, which comprises a catalytically active composition comprising vanadium, phosphorus and oxygen and has an essentially hollow cylindrical structure, wherein the hollow cylindrical structure has (a) a ratio of the height h to the diameter of the continuous hole $d_2$ of not more than 1.5 and (b) a ratio of the geometric surface area $A_{geo}$ to the geometric volume $V_{geo}$ of at least 2 mm$^{-1}$.

For the purposes of the present invention, an essentially hollow cylindrical structure is a structure which essentially comprises a cylinder having a continuous hole going through from one end face to the other. The cylinder has two essentially parallel end faces and an outer curved surface, with the cross section of the cylinder, i.e. parallel to the end faces, being essentially circular. The cross section of the continuous hole, i.e. parallel to the end faces of the cylinder, is likewise essentially circular. The continuous hole is preferably located centrally in the end faces, but other spatial arrangements are not excluded.

The term "essentially" indicates that deviations from the ideal geometry, for example slight deformations of the circular structure, end faces which are not perfectly parallel, chipped corners and edges, surface roughness or notches in the outer curved surface, the end faces or the internal surface of the continuous hole are allowed for in the catalyst of the present invention. Within the accuracy of tableting technology, circular end faces, a circular cross section of the continuous hole, parallel end faces and macroscopically smooth surfaces are preferred.

The essentially hollow cylindrical structure can be described by an external diameter $d_1$, a height h as the distance between the two end faces and a diameter of the internal hole (continuous hole) $d_2$. The three parameters mentioned are in each case the mean values for the hollow cylinder. This applies particularly in the case of deviations from the ideal geometry.

The catalyst of the present invention has a ratio of the height h to the diameter of the continuous hole $d_2$ of not more than 1.5. The ratio $h/d_2$ is preferably from 0.5 to 1.5, particularly preferably from 1.0 to 1.5.

As a further characteristic property, the catalyst has a ratio of the geometric surface area $A_{geo}$ to the geometric volume $V_{geo}$ of at least 2 mm$^{-1}$. For the purposes of the present invention, the geometric surface area $A_{geo}$ is the calculated surface area of all exposed surfaces of the hollow cylinder, including the internal curved surface of the continuous hole, on the basis of the abovementioned parameters $d_1$, h and $d_2$. The geometric volume $V_{geo}$ is the calculated volume of the hollow cylinder on the basis of the abovementioned parameters $d_1$, h and $d_2$. In the calculation of both quantities, no account is therefore taken of either pores or, for instance, notches or roughness in the exposed surfaces. The ratio $A_{geo}/V_{geo}$ is preferably from 2 to 3 mm$^{-1}$, particularly preferably from 2 to 2.5 mm$^{-1}$.

In a preferred embodiment, the catalyst of the present invention additionally has a ratio of the geometric volume $V_{geo}$ of the hollow cylindrical structure to the theoretical volume $V_{overall}$ of a corresponding solid cylinder having the same height h and the same external diameter $d_1$ of not more than 0.85. Here, the theoretical volume $V_{overall}$ of a corresponding solid cylinder having the same height h and the same external diameter $d_1$ is likewise determined mathematically on the basis of the abovementioned parameters $d_1$ and h. The ratio $V_{geo}/V_{overall}$ is particularly preferably from 0.3 to 0.85, very particularly preferably from 0.6 to 0.85, in particular from 0.7 to 0.85.

The external diameter $d_1$ of the catalyst of the present invention is preferably from 3 to 10 mm, particularly preferably from 4 to 8 mm, very particularly preferably from 5 to 6 mm. The height h is preferably from 1 to 10 mm, particularly preferably from 2 to 6 mm, very particularly preferably from 2 to 3 mm. The diameter of the continuous hole $d_2$ is preferably from 1 to 8 mm, particularly preferably from 2 to 6 mm, very particularly preferably from 2 to 3 mm.

The catalysts of the present invention comprise an oxygen-containing vanadium-phosphorus compound or a mixture of such compounds as catalytically active composition. Suitable active compositions are described, for example, in the patents U.S. Pat. No. 5,275,996, U.S. Pat. No. 5,641,722, U.S. Pat. No. 5,137,860, U.S. Pat. No. 5,095,125 or U.S. Pat. No. 4,933,312.

The catalysts of the present invention may further comprise promoters. Suitable promoters are the elements of the 1st to 15th groups of the Periodic Table and their compounds. Examples of suitable promoters are described in the published specifications WO 97/12674 and WO 95/26817 and in the patents U.S. Pat. Nos. 5,137,860, 5,296,436, 5,158,923 and 4,795,818. Preferred promoters are compounds of the elements cobalt, molybdenum, iron, zinc, hafnium, zirconium, lithium, titanium, chromium, manganese, nickel, copper, boron, silicon, antimony, tin, niobium and bismuth, particularly preferably molybdenum, iron, zinc, antimony, bismuth and lithium. The promoted catalysts of the present invention may comprise one or more promoters. The total content of promoters in the finished catalyst is generally not more than about 5% by weight, in each case calculated as oxide.

The catalysts of the present invention may further comprise auxiliaries such as tableting aids or pore formers.

Tableting aids are generally added when shaping of the catalysts of the present invention is carried out by means of tableting. Tableting aids are generally catalytically inert and improve the tableting properties of the precursor powder which is an intermediate in catalyst production, for example by improving the sliding properties and powder flow properties. A suitable and preferred tableting aid is graphite. The tableting aids added generally remain in the activated catalyst. The content of tableting aids in the finished catalyst is typically from about 2 to 6% by weight.

Pore formers are substances which are used to generate a defined pore structure in the macropore range. Their possible use is in principle independent of the shaping method. In general, they are compounds comprising carbon, hydrogen, oxygen and/or nitrogen which are added prior to shaping the catalyst and are mostly removed again by sublimation, decomposition and/or vaporization in the subsequent activation of the catalyst. Nevertheless, the finished catalyst may contain residues or decomposition products of the pore former.

In the catalysts of the present invention, the active composition comprising vanadium, phosphorus and oxygen may be present, for example, in pure, undiluted form as "all-active catalyst" or diluted with a preferably oxidic support material as "mixed catalyst". Examples of suitable support materials for the mixed catalysts are aluminum oxide, silicon dioxide, aluminosilicates, zirconium dioxide, titanium dioxide or mixtures thereof. Preference is given to all-active and mixed catalysts, particularly preferably all-active catalysts.

The catalysts of the present invention preferably have a phosphorus/vanadium atomic ratio of from 0.9 to 1.5, particularly preferably from 0.9 to 1.2 and very particularly preferably from 1.0 to 1.1. The mean oxidation state of the vanadium is preferably from +3.9 to +4.4 and particularly preferably from 4.0 to 4.3. The catalysts of the present invention preferably have a BET surface area of from 10 to 50 m$^2$/g and particularly preferably from 15 to 30 m$^2$/g. They preferably have a pore volume of from 0.1 to 0.5 ml/g and particularly preferably from 0.1 to 0.3 ml/g. The bulk density of the catalysts of the present invention is preferably from 0.5 to 1.5 kg/l and particularly preferably from 0.5 to 1.0 kg/l.

The catalysts of the present invention can be produced, for example, as described in the patents U.S. Pat. No. 5,275,996 and U.S. Pat. No. 5,641,722 or the published specification WO 97/12674, with shaping naturally being carried out so as to give the hollow cylindrical structure according to the present invention. Shaping is preferably carried out by tableting.

The main steps in the preferred method of producing the catalyst, encompassing formation of a precursor powder, shaping and subsequent activation, are described below.

a) Reaction of a pentavalent-vanadium compound (e.g. $V_2O_5$) with an organic, reducing solvent (e.g. an alcohol such as isobutanol) in the presence of a pentavalent phosphorus compound (e.g. orthophosphoric and/or pyrophosphoric acid) with heating. If desired, this step can be carried out in the presence of a dispersed, pulverulent support material. Preference is given to carrying out the reaction without addition of support material.

b) Isolation of the resulting vanadium-, phosphorus- and oxygen-containing catalyst precursor ("VPO precursor"), e.g. by filtration or evaporation.

c) Drying of the VPO precursor, if desired commencement of preactivation by additional elimination of water from the VPO precursor. Pulverulent support material and/or a pore former, for example stearic acid, cellulose or paraffins, can, if desired, then be mixed into the dried VPO precursor powder. Preference is given to further processing without addition of a support material.

d) Shaping by conversion into the essentially hollow cylindrical structure according to the present invention. Shaping is preferably carried out by tableting, advantageously with prior mixing-in of a lubricant such as graphite.

e) Preactivation of the shaped VPO precursor by heating in an atmosphere comprising oxygen, nitrogen, noble gases, carbon dioxide, carbon monoxide and/or water vapor. The mechanical and catalytic properties of the catalyst can be influenced by appropriate combinations of temperatures, treatment times and gas atmospheres matched to the respective catalyst system.

A less preferred alternative to tableting is, for example, extrusion. In this variant, the VPO precursor obtained in (b) is, for example, mixed with liquid to obtain an extrudable mass. This can then be extruded to form the hollow cylindrical structure according to the present invention. After drying, preactivation can then be carried out as described in (e).

It is also possible to treat the powder as described under (a) to (c) and (e) first and only then convert the preactivated powder into a paste and extrude it. After extrusion, the shaped bodies are dried or heat-treated again.

In a particularly preferred embodiment for producing the catalyst, vanadium pentoxide powder $V_2O_5$ is added to isobutanol and the mixture is admixed with the amount of phosphoric acid necessary to set the desired phosphorus/vanadium atomic ratio. The mixture is subsequently heated to form the VPO catalyst precursor by reduction of the vanadium and reaction with the phosphoric acid. The precursor is isolated by, for example, filtration, washed if necessary and dried at above 100° C. and, if appropriate, preactivated. The precursor powder obtained is then mixed with a lubricant, preferably graphite, and possibly a pore former, for example stearic acid, and converted into the hollow cylindrical structure having the geometry according to the present invention by tableting. The shaped bodies are then preactivated by heating in an atmosphere comprising oxygen, nitrogen, noble gases, carbon dioxide, carbon monoxide and/or water vapor.

The catalysts of the present invention are distinguished by their particular hollow cylindrical structure and the particular geometric conditions. They can easily be produced from active compositions known per se and when used in heterogeneously catalyzed gas-phase oxidation display a low pressure drop combined with sufficiently high mechanical stability. Furthermore, they have a large geometric surface area per unit geometric volume, which leads to a decisive advantage in terms of activity and selectivity. The continuous hole also saves active composition and reduces the bulk density.

Compared to the previously described geometries, the catalysts of the present invention have decisive advantages, in particular over

| | |
|---|---|
| pellets (solid cylinders): | less active composition |
| | lower bulk density |
| | higher activity |
| | higher selectivity |
| | lower pressure drop |
| hollow cylinders having previously described geometries: | higher activity |
| | higher selectivity |
| trilobes, tristars: | simpler production |
| | higher stability. |

The invention further provides a process for preparing maleic anhydride by heterogeneously catalyzed gas-phase oxidation of a hydrocarbon having at least four carbon atoms by means of oxygen-containing gases using the catalyst of the present invention.

Reactors used are generally shell-and-tube reactors. A shell-and-tube reactor comprises at least one reactor tube which is surrounded by a heat transfer medium for heating and/or cooling. In general, the shell-and-tube reactors used in industry contain from a few hundred to tens of thousands of parallel reactor tubes.

The shell-and-tube reactors can have one or more preheating zones which heat the inflowing gas mixture. A preheating zone integrated into a shell-and-tube reactor can be realized, for example, by means of reactor tubes filled with inert material and likewise surrounded by heat transfer medium. Suitable inert materials are in principle all shaped bodies which are chemically inert, i.e. neither induce nor catalyze any heterogeneously catalyzed reaction, and which display a maximum pressure drop below the maximum tolerable, plant-specific value in each case. Examples of suitable inert materials are oxidic materials such as $Al_2O_3$, SiC or metallic materials such as stainless steel. Examples of shaped bodies are spheres, pellets, hollow cylinders, rings, trilobes, tristars, wagon wheels, extrudates or irregular crushed bodies.

Hydrocarbons which are suitable for use in the process of the present invention are aliphatic and aromatic, saturated and unsaturated hydrocarbons having at least four carbon atoms, for example 1,3-butadiene, 1-butene, cis-2-butene, trans-2-butene, n-butane, a $C_4$-mixture, 1,3-pentadiene, 1,4-pentadiene, 1-pentene, cis-2-pentene, trans-2-pentene, n-pentane, cyclopentadiene, dicyclopentadiene, cyclopentene, cyclopentane, a $C_5$ mixture, hexenes, hexanes, cyclohexane and benzene. Preference is given to using 1-butene, cis-2-butene, trans-2-butene, n-butane, benzene or mixtures thereof. Particular preference is given to using n-butane and n-butane-containing gases and liquids. The n-butane used can, for example, originate from natural gas, from steam crackers or FCC plants.

The hydrocarbon is generally introduced in a quantity-regulated manner, i.e. with continual specification of a defined quantity per unit time. The hydrocarbon can be metered in in liquid or gaseous form. Preference is given to metered addition in liquid form with subsequent vaporization prior to entry into the shell-and-tube reactor.

As oxidants, use is made of oxygen-containing gases such as air, synthetic air, an oxygen-enriched gas or "pure" oxygen, e.g. oxygen from fractionation of air. The oxygen-containing gas is also introduced in a quantity-regulated manner.

The gas to be passed through the shell-and-tube reactor generally comprises inert gas. The proportion of inert gas at the beginning is usually from 50 to 95% by volume. Inert gases are all gases which do not contribute directly to formation of maleic anhydride, for example nitrogen, noble gases, carbon monoxide, carbon dioxide, water vapor, oxygenated and nonoxygenated hydrocarbons having less than four carbon atoms (e.g. methane, ethane, propane, methanol., formaldehyde, formic acid, ethanol, acetaldehyde, acetic acid, propanol, propionaldehyde, propionic acid, acrolein, crotonaldehyde) and mixtures thereof. In general, the inert gas is introduced into the system via the oxygen-containing gas. However, it is also possible to introduce further inert gases separately. Enrichment with further inert gases which can, for example, originate from the partial oxidation of the hydrocarbons is possible by means of partial recirculation of the output from the reactor, if appropriate after work-up.

To ensure a long catalyst life and further increases in conversion, selectivity, yield, space velocity over the catalyst and space-time yield, a volatile phosphorus compound is preferably fed into the gas in the process of the present invention. Its concentration at the beginning, i.e. at the reactor inlet, is at least 0.2 ppm by volume, i.e. $0.2 \times 10^{-6}$ parts by volume of the volatile phosphorus compounds, based on the total volume of the gas at the reactor inlet. Preference is given to a content of from 0.2 to 20 ppm by volume, particularly preferably from 0.5 to 10 ppm by volume. For the purposes of the present invention, volatile phosphorous compounds are all phosphorus-containing compounds which are present in gaseous form in the desired concentration under the use conditions. Examples which may be mentioned are the compounds of the formulae (I) and (II)

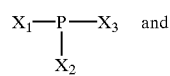

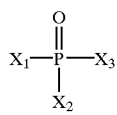

where $X^1$, $X^2$ and $X^3$ are, independently of one another, hydrogen, halogen, $C_1$–$C_6$-alkyl, $C_3$–$C_6$-cycloalkyl, $C_6$–$C_{10}$-aryl, $C_1$–$C_6$-alkoxy, $C_3$–$C_6$-cycloalkoxy or $C_6$–$C_{10}$-aroxy. Preference is given to compounds of the formula (III)

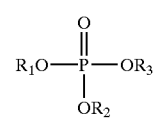

where $R^1$, $R^2$ and $R^3$ are, independently of one another, hydrogen, $C_1$–$C_6$-alkyl, $C_3$–$C_6$-cycloalkyl or $C_6$–$C_{10}$-aryl. Particular preference is given to compounds of the formula (III) in which $R^1$, $R^2$ and $R^3$ are, independently of one another, $C_1$–$C_4$-alkyl, for example methyl, ethyl, propyl, 1-methylethyl, butyl, 1-methylpropyl, 2-methylpropyl or 1,1-dimethylethyl. Very particular preference is given to trimethyl phosphate, triethyl phosphate and tripropyl phosphate, in particular triethyl phosphate.

The process of the present invention is generally carried out at from 350 to 480° C. The temperature specified is the temperature at which the catalyst bed present in the shell-and-tube reactor would be if the process were carried out in the absence of a chemical reaction. If this temperature is not exactly equal at all points, the term refers to the arithmetic mean of the temperatures along the reaction zone. In particular, this means that the true temperature at the catalyst can also be outside the specified range owing to the exothermic nature of the oxidation reaction. The process of the present invention is preferably carried out at from 380 to 460° C., particularly preferably from 380 to 430° C.

The process of the present invention can be carried out either at a pressure below atmospheric pressure (e.g. down to 0.05 MPa abs) or at above atmospheric pressure (e.g. up to 10 MPa abs). For the purposes of the present invention, this is the pressure prevailing in the shell-and-tube reactor unit. Preference is given to a pressure of from 0.1 to 1 MPa abs, particularly preferably from 0.1 to 0.5 MPa abs.

With regard to the use of the catalyst of the present invention in the process of the present invention, different variants are possible. In the simplest case, the shell-and-tube reactor is filled with a single, uniform catalyst charge. Here, the term catalyst charge refers to catalyst material which all has the same average composition and the same average activity per unit volume. A catalyst charge can be composed of the catalyst of the present invention or a mixture of at least one catalyst according to the present invention and further catalysts according to the present invention and/or catalysts not according to the present invention, with the catalyst charge also being able to be mixed with an inert material, i.e. be "diluted". In another variant, two or more successive catalyst charges are used in the shell-and-tube reactor. Thus, for example, it is possible and may be advantageous to use a less active catalyst charge in the vicinity of the reactor inlet and to use a more active catalyst charge downstream of the first catalyst charge.

The process of the present invention can be carried out in two preferred process variants, namely the "single pass" variant and the "recirculation" variant.

a) "Single Pass"

In the "single pass" variant, the conversion of hydrocarbons per pass through the reactor is from 75 to 95% and maleic anhydride and possibly oxygenated hydrocarbon by-products are removed from the output from the reactor, with the reaction gas passed through the reactor, in particular the unreacted hydrocarbons, not being directly recirculated. The total conversion of hydrocarbons per pass through the reactor is preferably from 80 to 90%. The remaining gas stream, which comprises inert gases, unreacted hydrocarbons and possibly further components which have not been separated off, is generally discharged from the plant.

The concentration of hydrocarbons at the beginning, i.e. at the reactor inlet, is preferably from 1.0 to 4.0% by volume, particularly preferably from 1.5 to 3.0% by volume. The concentration of oxygen at the beginning is preferably from 5 to 50% by volume, particularly preferably from 15 to 30% by volume. The origin of the oxygen used in the process of the present invention is in principle of no importance, as long as no interfering impurities are present. Out of simple industrial considerations, air is preferred as oxygen source. This can in the simplest case be used directly or preferably after removal of particles. Enrichment with oxygen, for example by liquefaction of air and subsequent distillation or pressure swing adsorption, is possible in principle.

The space velocity of hydrocarbons over the catalyst is generally at least 20 standard l/l·h, preferably at least 30 standard l/l·h, particularly preferably at least 35 standard l/l·h.

Maleic anhydride can be separated off by, for example, absorption in a suitable absorption medium. Suitable absorption media are, for example, water or organic liquids. In the case of absorption in water, maleic anhydride is hydrated to maleic acid. Preference is given to absorption in an organic solvent. Suitable organic solvents are, for example, the high-boiling solvents mentioned in WO 97/43242, e.g. tricresyl phosphate, dibutyl maleate, high molecular weight wax, aromatic hydrocarbons having a boiling point above 140° C. and di-$C_4$–$C_8$-alkyl phthalates such as dibutyl phthalate. Oxygenated hydrocarbon by-products are generally also absorbed in the solvents mentioned. The absorption can be carried out, for example, at from 60 to 160° C. and a pressure of from 0.1 to 0.5 MPa abs or above. Suitable methods are, for instance, passing the gaseous, cooled or uncooled output from the reactor through a container filled with absorption liquid or spraying the absorption liquid into the gas stream. Appropriate methods of scrubbing gas streams are known to those skilled in the art.

b) "Recirculation"

In the "recirculation" variant, the conversion of hydrocarbons per pass through the reactor is from 30 to 60%, maleic anhydride and possibly oxygenated hydrocarbon by-products are removed from the output from the reactor and at least part of the remaining stream or at least part of the unreacted hydrocarbons, which may have been separated off, is recirculated to the reaction zone. The total conversion of hydrocarbons per pass through the reactor is preferably from 40 to 50%.

The concentration of hydrocarbons at the beginning, i.e. at the reactor inlet, is preferably at least 2.0% by volume, particularly preferably at least 2.5% by volume. The concentration of oxygen at the beginning is preferably from 5 to 60% by volume, particularly preferably from 15 to 50% by volume. The origin of the oxygen used in the process of the present invention is in principle of no importance, as long as no interfering impurities are present. Out of simple industrial considerations, the oxygen used generally comes from air, with enrichment of the oxygen usually being carried out. This can be carried out, for example, by liquefaction of air and subsequent distillation or pressure swing adsorption. Preference is given to using an oxygen-containing gas having an oxygen concentration of from 20 to 100% by volume.

The space velocity of hydrocarbons over the catalyst is generally at least 20 standard l/l·h, preferably at least 30 standard l/l·h, particularly preferably at least 35 standard l/l·h.

The integrated total conversion of hydrocarbons, i.e. the conversion based on the overall plant, in the process of the present invention carried out using the "recirculation" variant is from 80 to 100%, preferably from 90 to 100%.

Maleic anhydride can be separated off, for example, as described under (a).

The gas stream remaining after maleic anhydride has been separated off or at least the unreacted hydrocarbons present therein are at least partly recirculated to the reaction zones in the "recirculation" variant.

(i) When the gas stream is recirculated without enrichment in the hydrocarbons, it is advantageous to discharge part of the gas stream (purge stream) from the plant in order to counteract accumulation of impurities. The remaining gas stream can generally be recirculated to the reaction zones. The appropriate amount of consumed hydrocarbon and oxygen is added in the customary fashion.

(ii) To reduce, for example, the amount of inert gas to be recirculated, it may be advantageous to concentrate the hydrocarbons present. Depending on the type of hydrocarbons used, various methods may be considered. Examples which may be mentioned are condensation or adsorption on suitable adsorbents (e.g. in the form of a pressure swing adsorption or temperature swing adsorption). Thus, for example, it is possible to concentrate n-butane by adsorption on activated carbon or zeolites with subsequent desorption at reduced pressure and/or elevated temperature.

The "single pass" and "recirculation" variants represent two preferred specific cases of the process of the present invention. They in no way apply any limitation regarding other possible variants or any limitation to the process parameters mentioned as preferred.

The maleic anhydride obtained can be further processed to give γ-butyrolactone, tetrahydrofuran, 1,4-butanediol or mixtures thereof, for example by direct hydrogenation of maleic anhydride in the gas phase as described in WO 97/43234 or by hydrogenation of a maleic diester in the gas phase as described in WO 97/43242.

In a particularly preferred embodiment for preparing maleic anhydride, n-butane is used as starting hydrocarbon and the heterogeneously catalyzed gas-phase oxidation is carried out in a "single pass" over the catalyst of the present invention.

Air as gas comprising oxygen and inert gas is introduced at a quantity-regulated rate into the feed unit. n-Butane is likewise fed in at a quantity-regulated rate, but preferably in liquid form via a pump and vaporized in the gas stream. The ratio of the amounts of n-butane and oxygen fed in is generally set in accordance with the heat evolved in the reaction and the desired space-time yield and is therefore dependent on, for example, the type and amount of catalyst. As further component, trialkyl phosphate as volatile phosphorus compound is preferably added in a quantity-regulated manner to the gas stream. The volatile phosphorus compound can, for example, be added in undiluted form or diluted with a suitable solvent, for example water. The required amount of phosphorus compound is dependent on various parameters, for example the type and amount of catalyst or the temperatures and pressures in the plant, and has to be adapted for each system.

The gas stream is intimately mixed by passing through a static mixer and is heated by passing through a heat exchanger. The mixed and preheated gas steam is then fed to the shell-and-tube reactor in which the catalyst of the present invention is located. The temperature of the shell-and-tube reactor is regulated by means of a salt melt circuit. The temperature is preferably set so that a conversion per pass through the reactor of from 75 to 90% is achieved.

The product gas stream leaving the shell-and-tube reactor is cooled in a heat exchanger and passed to the unit for separating off the maleic anhydride. In the preferred embodiment, the latter unit comprises at least one apparatus for the absorptive removal of maleic anhydride and possibly the oxygenated hydrocarbon by-products. Suitable apparatuses are, for example, containers filled with an absorption liquid through which the cooled product gas is passed or apparatuses in which the absorption liquid is sprayed into the gas stream. The solution containing maleic anhydride is discharged from the plant for further processing or for isolation of the desired product. The remaining gas stream is likewise discharged from the plant and, if desired, passed to a unit for recovering the unreacted n-butane.

The process of the present invention using the catalysts of the present invention makes it possible to achieve a high space velocity of hydrocarbon over the catalyst combined with a high conversion, a high selectivity, a high yield and therefore also a high space-time yield of maleic anhydride.

Definitions

The parameters referred to in this text are, unless indicated otherwise, defined as follows:

$$\text{geometric surface area } A_{geo} = \left(\frac{d_1^2 - d_2^2}{2}\right)\pi + (d_1 + d_2)\pi h$$

$$\text{geometric volume } V_{geo} = \left(\frac{d_1^2 - d_2^2}{4}\right)\pi h$$

$$\text{theoretical volume of solid cylinder } V_{overall} = \left(\frac{d_1^2}{4}\right)\pi h$$

$$\text{space-time yield} = \frac{{}^m\text{maleic anhydride}}{V_{catalyst} \cdot t}$$

$$\text{space velocity} = \frac{V_{hydrocarbon}}{V_{catalyst} \cdot t}$$

$$\text{conversion } C = \frac{{}^n\text{hydrocarbon, reactor, in} - {}^n\text{hydrocarbon, reactor, out}}{{}^n\text{hydrocarbon, reactor, in}}$$

$$\text{selectivity } S = \frac{^n MA, \text{reactor, out}}{^n MA, \text{reactor, in} - {^n MA, \text{reactor, out}}}$$

$$\text{yield } A = C \cdot S$$

| | |
|---|---|
| $d_1$ | external diameter of the hollow cylinder or solid cylinder [mm] |
| $h$ | height of the hollow cylinder or solid cylinder [mm] |
| $d_2$ | diameter of the continuous hole [mm] |
| $A_{geo}$ | geometric surface area of the shaped body on the basis of the geometric parameters $d_1$, $h$ and $d_2$ [mm$^2$] |
| $V_{geo}$ | geometric volume of the shaped body on the basis of the geometric parameters $d_1$, $h$ and $d_2$ [mm$^3$] |
| $V_{overall}$ | theoretical volume of a corresponding solid cylinder having a height of $h$ and an external diameter of $d_1$ [mm$^3$] |
| $m_{maleic\ anhydride}$ | mass of maleic anhydride produced [g] |
| $V_{catalyst}$ | bed volume of catalyst summed over all reaction zones [l] |
| $t$ | time [h] |
| $V_{hydrocarbon}$ | volume standardized to 0° C. and 0.1013 MPa of the hydrocarbon in the gas phase [standard l] (Mathematical parameter. If a hydrocarbon is present as a liquid under these conditions, the hypothetical gas volume is calculated by means of the ideal gas rule.) |
| $C$ | conversion of hydrocarbons per pass through the reactor |
| $S$ | selectivity in respect of maleic anhydride per pass through the reactor |
| $Y$ | yield of maleic anhydride per pass through the reactor |
| $n_{hydrocarbon, reactor, in}$ | molar flow of hydrocarbons at the reactor inlet [mol/h] |
| $n_{hydrocarbon, reactor, out}$ | molar flow of hydrocarbons at the reactor outlet [mol/h] |
| $n_{hydrocarbon, plant, in}$ | molar flow of hydrocarbons at the inlet to the plant [mol/h] |
| $n_{hydrocarbon, plant, out}$ | molar flow of hydrocarbons at the outlet from the plant [mol/h] |
| $n_{MA, reactor, out}$ | molar flow of maleic anhydride at the reactor outlet [mol/h] |
| $n_{MA, plant, out}$ | molar flow of maleic anhydride at the outlet from the plant [mol/h] |

EXAMPLES

Catalysts A to F

In a 240 l vessel, 11.8 kg of 100% strength orthophosphoric acid were dissolved in 150 l of isobutanol while stirring and 9.09 kg of vanadium pentoxide were subsequently added. This suspension was refluxed for 16 hours and then cooled to room temperature. The precipitate which had been formed was filtered off, washed with isobutanol and dried at 150° C. under reduced pressure at 8 kPa (80 mbar). The dried powder was subsequently treated at 250–300° C. for 2 hours in a rotary tube. After cooling to room temperature, 3% by weight of graphite were added and the powders were intimately mixed.

The powder was subsequently tabletted to form hollow cylinders having different geometries.

After shaping, the hollow cylinders of various geometries were heated in a muffle furnace in air, firstly at 7° C./min to 250° C. and subsequently at 2° C./min to 350° C. The catalyst was held at this temperature for 10 minutes, before the atmosphere was changed from air to $N_2/H_2O$ (1:1). Under this $N_2/H_2O$ atmosphere (1:1), the hollow cylinders were heated to 425° C. and the system was held at this temperature for 3 hours. Finally, the catalysts were cooled to room temperature under nitrogen.

Table 1 gives an overview of the geometric and physicochemical properties of the catalysts produced.

Plant

The experimental plant was equipped with a feed unit and a reactor tube. A shell-and-tube reactor can be readily replaced by a reactor tube on a laboratory or pilot plant scale as long as the dimensions of the reactor tube are in the region of those of an industrial reactor tube. The plant was operated in a "single pass".

The hydrocarbon was introduced in liquid form via a pump at a quantity-regulated rate. As oxygen-containing gas, air was introduced at a quantity-regulated rate. Triethyl phosphate (TEP), dissolved in water, was likewise introduced in liquid form at a quantity-regulated rate.

The shell-and-tube reactor unit comprised a shell-and-tube reactor having one reactor tube. The length of the reactor tube was 6.5 m and the internal diameter was 22.3 mm. The interior of the reactor tube was provided with a multithermocouple having 20 temperature measurement points located in a protective tube. The reactor tube was surrounded by a circulated heat transfer medium whose temperature could be regulated. The reaction gas mixture flowed through the reactor tube from the top downward. The upper 0.3 m of the reactor tube was filled with inert material and formed the preheating zone. The reaction zone contained 2.2 l of catalyst. The heat transfer medium used was a salt melt.

Immediately downstream of the shell-and-tube reactor unit, gaseous product was taken off and analyzed on-line by gas chromatography. The main stream of the gaseous output from the reactor was discharged from the plant.

Examples 1 to 6

All examples were carried out using n-butane as hydrocarbon. The results obtained are summarized in Table 2.

To enable the experiments to be compared, a conversion of about 85% was set by means of the salt bath temperature $T_{SB}$. The experiments show that the comparative catalysts E* and F*, which have an $A_{geo}/V_{geo}$ ratio of less than 2 mm$^{-1}$ (comparative catalyst E*) or an $h/d_2$ ratio of greater than 1.5 (comparative catalyst F*), lead to a significantly lower selectivity, yield and space-time yield than do the catalysts A to D according to the present invention.

TABLE 1

Overview of the geometric and physicochemical properties of the catalysts produced

| Example/ Catalyst | $d_1$ [mm] | h [mm] | $d_2$ [mm] | $A_{geo}/V_{geo}$ [mm$^{-1}$] | $h/d_2$ | $V_{geo}/V_{overall}$ | $V_{ox.}$ | BET [m$^2$/g] | Density [kg/l] |
|---|---|---|---|---|---|---|---|---|---|
| 1/A | 5 | 3 | 2 | 2.00 | 1.5 | 0.84 | 4.21 | 23 | 0.70 |
| 2/B | 5 | 3 | 2.5 | 2.27 | 1.2 | 0.75 | 4.10 | 23 | 0.65 |
| 3/C | 5 | 3 | 3 | 2.67 | 1.0 | 0.64 | 4.28 | 20 | 0.59 |
| 4/D | 6 | 3 | 3 | 2.00 | 1.0 | 0.75 | 4.21 | n.d. | 0.68 |
| 5*/E* | 8 | 5 | 5 | 1.73* | 1.0 | 0.61 | 4.13 | 31 | 0.52 |
| 6*/F* | 4 | 4 | 1.2 | 2.18 | 3.3* | 0.84 | 4.15 | 21 | 0.80 |

*Comparative example/comparative catalyst
n.d.: not determined

TABLE 2

Overview of the geometric and catalytic properties of the catalysts tested

| Example/ Catalyst | $d_1$ [mm] | h [mm] | $d_2$ [mm] | $T_{SB}$ [° C.] | $T_{HS}$ [° C.] | Δp [MPa] | Conversion C [%] | Selectivity S [%] | Yield A [%] | Space-time yield [g/l · h] |
|---|---|---|---|---|---|---|---|---|---|---|
| 1/A | 5 | 3 | 2 | 410 | 434 | 0.15 | 84.9 | 65.0 | 55.2 | 97 |
| 2/B | 5 | 3 | 2.5 | 410 | 434 | 0.13 | 85.1 | 67.3 | 57.3 | 100 |
| 3/C | 5 | 3 | 3 | 400 | 429 | 0.12 | 85.0 | 63.4 | 53.9 | 94 |
| 4/D | 6 | 3 | 3 | 400 | 429 | 0.11 | 85.0 | 64.8 | 55.1 | 96 |
| 5*/E* | 8 | 5 | 5 | 420 | n.d. | 0.07 | 85.4 | 55.0 | 47.0 | 82 |
| 6*/F* | 4 | 4 | 1.2 | 405 | 440 | 0.16 | 85.1 | 60.2 | 51.2 | 90 |

*Comparative example/comparative catalyst
n.d.: not determined

We claim:

1. A catalyst for preparing maleic anhydride by heterogeneously catalyzed gas-phase oxidation of a hydrocarbon having at least four carbon atoms, which comprises a catalytically active composition comprising vanadium, phosphorus and oxygen and has an essentially hollow cylindrical structure, wherein the hollow cylindrical structure has (a) a ratio of the height h to the diameter of the continuous hole $d_2$ of not more than 1.5 and (b) a ratio of the geometric surface area $A_{geo}$ to the geometric volume $V_{geo}$ of at least 2 mm$^{-1}$.

2. A catalyst as claimed in claim 1, wherein the ratio of the geometric volume $V_{geo}$ of the hollow cylindrical structure to the theoretical volume $V_{overall}$ of a corresponding solid cylinder having the same height h and the same external diameter $d_1$ is not more than 0.85.

3. A catalyst as claimed in claim 1, wherein the external diameter $d_1$ is from 3 to 10 mm, the height h is from 1 to 10 mm and the diameter of the internal hole $d_2$ is from 1 to 8 mm.

4. A catalyst as claimed in claim 1, wherein the phosphorus/vanadium atomic ratio is from 0.9 to 1.5, the mean oxidation state of the vanadium is from +3.9 to +4.4, the BET surface area is from 10 to 50 m$^2$/g, the pore volume is from 0.1 to 0.5 ml/g and the bulk density is from 0.5 to 1.5 kg/l.

5. A process for preparing maleic anhydride by heterogeneously catalyzed gas-phase oxidation of a hydrocarbon having at least four carbon atoms by means of oxygen-containing gases, wherein a catalyst as claimed in claim 1 is used.

6. A process as claimed in claim 5, wherein the heterogeneously catalyzed gas-phase oxidation is carried out in a shell-and-tube reactor at from 350 to 480° C. and a pressure of from 0.1 to 1.0 MPa abs.

7. A process as claimed in claim 5, wherein the hydrocarbon used is n-butane.

8. A process as claimed in claim 5, wherein the heterogeneously catalyzed gas-phase oxidation is carried out in the presence of a volatile phosphorus compound.

9. A catalyst as claimed in claim 1, wherein the ratio of h to $d_2$ is from 0.5 to 1.5.

10. A catalyst as claimed in claim 1, wherein the ratio h to $d_2$ is from 1 to 1.5.

11. A catalyst as claimed in claim 1, wherein the ratio of $A_{geo}$ to $V_{geo}$ is from 2 to 3 mm$^{-1}$.

12. A catalyst as claimed in claim 1, wherein the ratio of $A_{geo}$ to $V_{geo}$ is from 2 to 2.5 mm$^{-1}$.

* * * * *